(12) United States Patent
Bernard et al.

(10) Patent No.: US 7,999,008 B2
(45) Date of Patent: *Aug. 16, 2011

(54) UREA COMPOUNDS THAT PROMOTE DESQUAMATION

(75) Inventors: Dominique Bernard, Paris (FR); Lucie Simonetti, Vincennes (FR); Pascale Pelletier, Antony (FR)

(73) Assignee: L'Oreal, Paris (FR)

( * ) Notice: Subject to any disclaimer, the term of this patent is extended or adjusted under 35 U.S.C. 154(b) by 481 days.

This patent is subject to a terminal disclaimer.

(21) Appl. No.: 11/485,506

(22) Filed: Jul. 13, 2006

(65) Prior Publication Data

US 2007/0014748 A1    Jan. 18, 2007

Related U.S. Application Data

(60) Provisional application No. 60/724,951, filed on Oct. 11, 2005.

(30) Foreign Application Priority Data

Jul. 13, 2005 (FR) ...................................... 05 52189

(51) Int. Cl.
*A61K 8/02* (2006.01)
*A61K 31/17* (2006.01)
*A01N 47/28* (2006.01)

(52) U.S. Cl. ........................................ 514/588; 424/401

(58) Field of Classification Search ........................ None
See application file for complete search history.

(56) References Cited

U.S. PATENT DOCUMENTS

2003/0021379 A1    2/2003   Fein
2004/0197299 A1*  10/2004   Delattre et al. ............ 424/78.02
2005/0113268 A1*   5/2005   Landa et al. .................. 510/130

FOREIGN PATENT DOCUMENTS

EP    1 535 607 A1    6/2005
FR    2 816 837       5/2002

OTHER PUBLICATIONS

National Starch [online] retrieved from: http://news.nationalstarch.com/NewsStory.asp?newsItemId=416 on Mar. 20, 2009. Dec. 3, 2003. 3 pages.*
Formulating with Hydrovance [online] retrieved from: http://www.personalcarepolymers.com/PCP/Products/ProductOverview.htm?id=95 on Mar. 20, 2009. May 17, 2005. 7 pages.*
English language machine translation of DE2703185; Aug. 1978; 7 pages.*
Derivative [online] merriam websters online dictionary retrieved from http://.merriam-webster.com/cgi-bin/dictionary?book=dictionary&va=derivative; Jul. 5, 2008; 1 page.*
Anonymous: "pH Stability of Hydroxyalkylurea in Combination Either with One or More of a Cyclic (lactone) and/or Acylic Ester," Dec. 22, 2004, IP. Com Journal, IP. Com. Inc., West Henrietta, NY, US, XP013022595.
M. Ponec, et al. "Lack of Desquamation—the Achilles Heel of the Reconstructed Epidermis" International Journal of Cosmetic Science, 2002, vol. 24, (pp. 263-272).
Sebastien Niamke, et al, "Physico-Chemical and Immunological Properties and Partial Amino Acid Sequencing of a New Metalloprotease: Endoprotease Thr-N" Biochimica et Biophysica Acta, vol. 1623 (2003), (pp. 21-28), www.sciencedirect.com.
D. Bernard, et al. "Analysis of Proteins with Caseinolytic Activity in a Human Stratum Corneum Extract Revealed a Yet Unidentified Cysteine Protease and Identified the So-Called "Stratum Corneum Thiol Protease" as Cathepsin L2" The Society for Investigative Dermatology. Inc, vol. 120, No. 4 (Apr. 2003), (pp. 592-600).

* cited by examiner

*Primary Examiner* — Ernst Arnold
(74) *Attorney, Agent, or Firm* — Oblon, Spivak, McClelland, Maier & Neustadt, L.L.P.

(57) ABSTRACT

The invention relates to the use of at least one urea derivative of the following formula (I)

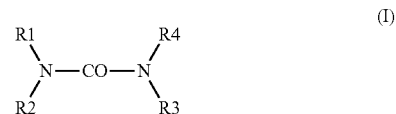

in a composition containing a physiologically acceptable medium, as agent intended for stimulating desquamation of the skin and/or the mucous membranes. It also relates to a method of cosmetic treatment and cosmetic agents containing it.

18 Claims, 1 Drawing Sheet

FIG. 1

UREA COMPOUNDS THAT PROMOTE DESQUAMATION

REFERENCE TO PRIOR APPLICATIONS

This application claims priority to U.S. provisional application 60/724,951 filed Oct. 11, 2005, and to French patent application 0552189 filed Jul. 13, 2005, both incorporated herein by reference.

FIELD OF THE INVENTION

The present invention relates to novel desquamation-promoting agents, and to their use in cosmetic or pharmaceutical, in particular, dermatological, compositions. It also relates to cosmetic methods for treating the skin or its annexes, and compositions allowing their use.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

The skin has two compartments, one which is superficial, the epidermis, and one which is deeper, the dermis, which interact. The natural human epidermis is mainly composed of three types of cell which are the keratinocytes, which form the great majority, the melanocytes and the Langerhans' cells.

The epidermis is conventionally divided into a basal layer of keratinocytes constituting the germinative layer of the epidermis, a so-called prickle cell layer consisting of several layers of polyhedral cells arranged on the germinative layers, one to three so-called granular layers consisting of flattened cells containing distinct cytoplasmic inclusions, the keratohyalin granules and finally the horny layer (or stratum corneum), consisting of a set of layers of keratinocytes at the final stage of their differentiation, called corneocytes. The corneocytes are anucleated cells mainly composed of a fibrous matrix containing cytokeratins, surrounded by a very resistant structure 15 nm thick, called horny or hornified envelope. The stacking of these corneocytes constitutes the horny layer which is responsible for the barrier function of the epidermis. During the normal desquamation process, the most superficial corneocytes become detached from the surface of the epidermis.

Intercellular structures derived from desmosomes, called corneosomes or corneodesmosomes, have been described in the horny layer. They are of major importance in intercorneocyte cohesion and in the desquamation process. In particular, a close correlation exists between cell dissociation and proteolysis of certain corneodesmosomal components such as desmoglein I or corneodesmosin.

Several trypsin or chymotrypsin type serine proteases appear to be involved in the proteolysis of the corneodesmosomes, in particular the chymotryptic enzyme of the horny layer (stratum corneum chymotryptic enzyme).

The dermis provides the epidermis with a solid support. It is also its feeder component. It consists mainly of fibroblasts and an extracellular matrix predominantly composed of collagen, elastin and a substance called ground substance. Leukocytes, mastocytes or tissue macrophages are also present. Finally, the dermis is crossed by blood vessels and nerve fibres.

The cohesion between the epidermis and the dermis is provided by the dermoepidermal junction.

The epidermal homeostasis corresponds to an equilibrium between the keratinocytes entering into differentiation in the deep layers of the epidermis and corneocytes removed from the surface of the epidermis in a process called desquamation. Normally, desquamation occurs corneocyte by corneocyte and remains imperceptible.

Desquamation has in the past been associated with mechanical actions. This so-called bricks and mortar theory, the bricks being the corneocytes linked to each other by a lipid mortar (P. Elias, 1984), was contradicted only by the discovery of cohesive structures derived from the desmosomes called corneodesmosomes linked to the horny envelope and to the intermediate filaments of keratins (Chapman, Walsh et al. 1991; Serre, Mils et al. 1991; Walsh and Chapman 1991). The proteins which constitute these structures are the substrates for the desquamation enzymes. Indeed, the gradual appearance of fragments of desmosomal proteins during differentiation and the apparent ultrastructural modifications of the desmosome have led researchers in the direction of enzymes responsible for these changes.

The first, T. Egelrud (Egelrud, Hofer et al. 1988; Egelrud and Lundstrom 1990; Egelrud and Lundstrom 1991), has demonstrated in the stratum corneum (SC) the existence of protease activities of the "trypsin-like" and especially "chymotrypsin-like" type associated with desquamation. These studies by T. Egelrud are part of the basic studies of any research relating to the bio-chemistry of desquamation. Subsequently, several cysteine and aspartic acid proteases were implicated in this process, in particular the stratum corneum thiol protease (SCTP) or cathepsin L2, the stratum corneum cathepsin L-like (SCCL) and cathepsin D.

In a number of situations, it may be desirable to stimulate this desquamation mechanism in order to promote epidermal renewal and improve the brightness of the complexion, attenuate surface irregularities and smoothe the skin, or to promote the cleansing action and the removal of dead cells at the surface of the body. In physiological states, thickening of the horny layer is also observed which it is desired to limit, for example in the case of callosites or after exposure to sunlight. Moreover, in some skin disorders, desquamation becomes visible and it is large sized scales containing numerous corneocytes which are removed. Deregulations of desquamation are increasingly better described at the molecular level and associated with aspects of abnormal skin.

Ichthyoses are generally examples of impaired epidermal differentiation associated with abnormal desquamation. In psoriasis, an inflammatory skin disease, and atopic dermatitis, it has also been possible to show disorders associated with abnormal desquamation. In the field of acne, the accumulation of a keratin plug (which can be removed by protease activities) obstructing the pores is one of the reasons for the appearance of comedones. The appearance of dandruff is another example of a desquamation defect where the scales are abnormally visible. The impaired desquamation which is generally present in reconstructed epidermes (Vicanova, Mommaas et al. 1996) also represents a proteolytic defect. Some pathological skins can benefit from prodesquamating treatment based on urea derivatives. Among these pathologies, there may be mentioned the Netherton syndrome, the Papillon-Lefèvre syndrome, more generally ichthyoses of genetic origin and psoriasis or atopic dermatitis and the like.

Various methods have already been proposed for promoting desquamation, in particular by peeling or scrubbing. It is also possible to use in particular retinoic acid and its derivatives, x-hydroxy acids, such as lactic acid or glycolic acid, or β-hydroxy acids, such as salicylic acid.

However, the active agents proposed, although they give good results, often have a proteolytic and/or keratolytic activity which may lead to irritation of the areas where they are applied. Moreover, the addition of exogenous protease to compositions can pose problems of stabilization, irritation and create an allergy risk for subjects to whom they are applied.

The prodesquamating properties of urea are generally associated with its protein-denaturing properties (so-called "keratolytic" effect). Urea is thought to denature certain corneodesmosomal substrates promoting, inter alia, the action of certain proteases. On the other hand, this effect is not a lasting effect capable of stimulating the natural desquamation processes because urea in the end, especially at concentrations greater than 2M, becomes denaturing for the proteases themselves. It would therefore be advantageous to find a compound capable of durably stimulating the proteolytic activities of the stratum corneum.

Some cosmetic active agents are capable of stimulating the degradation of the proteins of the corneodesmosome and therefore desquamation. Patent application EP 852 949 (Shiseido) describes the use, as desquamating agent, of derivatives of alpha-amino acids of the glycine type, which favour the degradation of desmoglein (corneodesmosome protein).

OBJECTS OF THE INVENTION

A need therefore still exists to have available agents stimulating desquamation of the skin or the mucous membranes, endowed with good activity without having the disadvantages of the compounds of the state of the art. A particular need exists to stimulate the natural desquamation processes, in particular by promoting the proteases associated with desquamation and naturally present in the skin.

SUMMARY OF THE INVENTION

Unexpectedly, it has been discovered that these objects and others are achieved by the use of certain compounds derived from urea of the following formula (I)

in which:

$R_1$, $R_2$, $R_3$ and $R_4$ each represent, independently of each other, a hydrogen atom, a $C_1$-$C_4$ alkyl group or a $C_2$-$C_6$ hydroxyalkyl group which optionally contains from 1 to 5 hydroxyl groups, where at least one of the radicals $R_1$ to $R_4$ represents a hydroxyalkyl group, and their salts, their solvates and their isomers.

DETAILED DESCRIPTION OF THE PREFERRED EMBODIMENTS

The invention thus relates to the use, etc., of certain compounds derived from urea of the following formula (I)

in which:

$R_1$, $R_2$, $R_3$ and $R_4$ each represent, independently of each other, a hydrogen atom, a $C_1$-$C_4$ alkyl group or a $C_2$-$C_6$ hydroxyalkyl group which optionally contains from 1 to 5 hydroxyl groups, where at least one of the radicals $R_1$ to $R_4$ represents a hydroxyalkyl group, and their salts, their solvates and their isomers in a composition containing a physiologically acceptable medium, as agent intended for stimulating desquamation of the skin and/or the mucous membranes and/or the superficial body growths.

Indeed, it has been discovered, in the context of the present invention, that such compounds have a remarkable effect on several mechanisms involved in desquamation, thus allowing a complete and natural action of stimulating this process, and the application in all cases where it is desirable to promote and/or accelerate the removal of the dead layers of the epidermis.

This use is cosmetic and non-therapeutic, and is aimed at improving the physical appearance and/or the aesthetic appearance of the individual whose desquamation and/or exfoliation and/or cell renewal is being stimulated.

For compounds of formula (I):
Preferably, $R_1$ denotes a $C_2$-$C_6$ hydroxyl group, and $R_2$, $R_3$ and $R_4$ denote, independently of each other, a hydrogen atom or a $C_1$-$C_4$ alkyl group;
Preferably, $R_1$ denotes a $C_2$-$C_6$ hydroxyalkyl group comprising from 1 to 5 hydroxyl groups, in particular 1 hydroxyl group, and $R_2$, $R_3$ and $R_4$ denote a hydrogen atom;
More preferably, $R_1$ denotes a $C_2$-$C_4$ hydroxyalkyl group comprising 1 hydroxyl group, and $R_2$, $R_3$ and $R_4$ denote a hydrogen atom.

Among the alkyl groups, there may be mentioned in particular methyl, ethyl, n-propyl, isopropyl, n-butyl, isobutyl and tert-butyl groups.

Among the hydroxyalkyl groups, those containing a single hydroxyl group are preferred, and in particular the hydroxyethyl, hydroxypropyl, hydroxybutyl, hydroxypentyl and hydroxyhexyl groups, are preferred.

Among the salts, there may be mentioned in particular the salts of inorganic acids, such as sulphuric acid, hydrochloric acid, hydrobromic acid, hydriodic acid, phosphoric acid and boric acid. There may also be mentioned the salts of organic acids, which may contain one or more carboxylic, sulphonic or phosphonic acid groups. They may be linear, branched or cyclic aliphatic acids or aromatic acids. These acids may additionally contain one or more heteroatoms chosen from O and N, for example in the form of hydroxyl groups. There may be mentioned in particular propionic acid, acetic acid, terephthalic acid, citric acid and tartaric acid.

The expression solvate is understood to mean a stoichiometric mixture of the said compound of formula (I) with one or more molecules of water or of organic solvent, such a mixture typically being obtained from the synthesis of the compound of formula (I).

As preferred compounds of formula (I), there may be mentioned N-(2-hydroxyethyl)urea; N-(2-hydroxypropyl)-urea; N-(3-hydroxypropyl)urea; N-(2,3-dihydroxypropyl)-urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(tris-hydroxymethylmethyl)urea; N-ethyl-N'-(2-hydroxyethyl) urea; N,N-bis(2-hydroxyethyl)urea; N,N'-bis(2-hydroxyethyl)urea; N,N-bis(2-hydroxypropyl)urea; N,N'-bis(2-hydroxypropyl)urea; N,N-bis(2-hydroxyethyl)-N'-propylurea; N,N-bis(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis(2-hydroxyethyl)-N',N'-dimethylurea; N,N,N',N'-tetrakis(2-hydroxyethyl)urea; N',N'-bis(2-hydroxyethyl)-N',N'-bis(2-hydroxypropyl)-urea; salts and solvates thereof, and mixtures thereof.

Preferably, the compound of formula (I) is N-(2-hydroxyethyl)urea.

The compounds of formula (I) are known compounds which are described in particular in application DE-A-2703185. Among these, N-(2-hydroxyethyl)urea is additionally commercially available, in the form of a mixture at 50% by weight in water, from the company NATIONAL STARCH under the trade name Hydrovance®. However, to the knowledge of the applicant, these compounds have never been proposed for stimulating proteolytic activities and promoting desquamation.

The quantity of N-(2-hydroxyethyl)urea and of any other compound of formula (I) used according to the invention depends on the desired result and in particular on the depth of the peeling or exfoliation which it is desired to obtain, which itself depends on the condition of the skin to be improved. The compound of formula (I) may be present in particular in the composition according to the invention in an amount ranging from 0.01% to 70% by weight and more, relative to the total weight of the composition, preferably greater than or equal to 0.1% by weight, or even greater than or equal to 1%; the concentrations can, in some embodiments, vary from 0.1% to 20% by weight, and will in particular preferably be less than or equal to 10% by weight, in particular for daily care applications.

Higher concentrations, in particular from about 30 to 50%, will be preferably used for peeling applications; these applications will be more spaced apart over time, for example weekly or every 2 weeks, in which the compounds of formula (I) will be removed from the application surface after a contact time, for example by rinsing the corresponding body surface. The contact time may vary for example from 5 min to 6 hours.

The compositions according to the invention may be cosmetic or pharmaceutical compositions, in particular dermatological compositions.

A physiologically acceptable medium is, according to the invention, a cosmetically or pharmaceutically acceptable medium compatible with the skin, the mucous membranes, the nails and/or the hair.

The compositions according to the invention may be applied to the nails, the hair and more particularly to the skin and the mucous membranes. It is preferably a cosmetically acceptable medium, that is to say which has a pleasant colour, odour and feel and which does not cause unacceptable discomfort.

The compositions are preferably cosmetic compositions or products. The expression "cosmetic product" is understood to mean in particular any substance or preparation intended to be brought into contact with the various superficial parts of the human body (epidermis, piliary and hair system, nails, lips and external genital organs) or with the teeth and the buccal mucous membranes, exclusively or mainly, to clean them, to perfume them, to modify the appearance thereof and/or to correct the body odours and/or to protect them or to maintain them in a good state (amended cosmetics directive 76/768/EEC).

Three properties were therefore studied:

The prodesquamating power, by the test of degradation of corneodesmosin in a controlled environment chamber with formulated products containing 5% active agent. This test makes it possible to evaluate the capacity of a formulated active agent to modulate the proteolytic degradation of corneodesmosin.

The "keratolytic" potential: The keratin solubilization ("keratolysis") test: This test corresponds to demonstrating the denaturing capacities of urea and its derivatives. The effect of the molecules on the solubilization of the keratins of the SC is monitored on an electrophoresis gel.

The "activating" potential of the acid proteases of the SC: This test makes it possible to show that under certain conditions, the proteolytic potential of certain epidermal proteases could be increased.

According to one of the aspects of the invention, the said compound of formula (I) has a corneodesmosin degrading effect which it stimulates.

According to another aspect of the invention, the said compound of formula (I) has a keratolytic effect greater than that of urea.

Finally, and advantageously, the compound of formula (I) as defined above stimulates the activity of proteases of the stratum corneum. These enzymes are chosen in particular from the group comprising:
  serine proteases of the kallikrein family, such as kallikrein 5, 7 or 14
  aspartic acid proteases such as cathepsin D, E or SASPase (Locuslink 151516), or the protease described in application WO 04/007548;
  cysteine proteases such as cathepsin B, H, L, L2, calpains or caspase 14;
  metaloproteases such as carboxypeptidases.

In particular, N-(2-hydroxyethyl)urea at a concentration of 0.5 to 2M, and in particular 1M, durably stimulates the degradation of a protein substrate by the acid proteases of the SC, such as cathepsin D or cathepsin L2.

The compositions according to the invention are in particular exfoliating compositions suitable for scrubbing the roughness of the skin. They may be peeling compositions which make it possible to remove a larger thickness of the horny layer such as calluses.

Compositions according to the invention are also compositions intended for cleansing the skin and/or the scalp, in which the action of the cleansing agents will be enhanced by promoting the removal of the dead cells from the surface cleansed.

According to another aspect of the invention, the composition containing the compound of formula (I) or its derivatives is a care composition intended to improve the surface state of the skin and/or the mucous membranes, in particular the lips; in particular the said composition will promote the removal of the roughness and/or of the dead skins present at the surface of the skin and/or the lips.

The invention also relates to the use of at least one compound of formula (I) or its derivatives as defined in the preceding text, for the preparation of a composition intended for the treatment of the signs associated with desquamation disorders.

The subject of the invention is also the use of at least one compound of formula (I) for the preparation of a composition intended for the treatment of at least one skin disorder chosen from ichthyosis, hyperkeratosis, xeroses, psoriasis, atopic dermatitis, acne and dandruff.

Xeroses are skin disorders in which there is deregulation of desquamation; there may be mentioned senile xeroses, winter xeroses, xeroses linked to the onset of menopause or to the use of certain detergents.

In the field of acne, the accumulation of a keratin plug obstructing the pores is one of the reasons for the appearance of comedones; the latter can be more easily removed, or its formation slowed or avoided, by the proteolytic and desquamating activities of the compounds according to the invention.

The appearance of dandruff is another example of a desquamation effect where the scales are abnormally visible.

According to one of the embodiments of the invention, the compositions are intended for promoting wound healing, by promoting the removal of debris and the like.

According to another embodiment, the compounds of formula I or the compositions containing them, as defined above, are useful for improving the appearance of the nails by removing the surface irregularities and by preparing them for the application of a care or makeup product. The retention of the varnish on the nail will in particular be promoted by the prior application of a compound of formula I, which will have a keratolytic and desquamating activity. The compounds of formula I or the compositions containing them will also promote the removal of the cuticles which may be present around the nail. The compounds of formula I may be applied in a base formulation during a 1st stage, and then after drying, the nail varnish will be optionally applied.

In general, any composition of the invention may be ingested, injected or applied to the skin (on any skin area of the body) or to the mucous membranes (buccal, jugal, gingival, genital, conjuctival and the like).

Preferably, a composition according to the invention is applied to the skin or the mucous membranes.

According to the mode of administration considered, it may be provided in any galenic form. For a topical application to the skin or the mucous membranes, the composition may have the form, in particular, of aqueous or oily solutions or of lotion or serum type dispersions, of emulsions having a liquid or semi-liquid consistency of the milk type, which are obtained by dispersing a fatty phase in an aqueous phase (O/W) or conversely (W/O), or of suspensions or emulsions having a soft consistency of the cream or aqueous or anhydrous gel type, or alternatively of microcapsules or microparticles, or of vesicular dispersions of the ionic and/or nonionic type or of foams. These compositions are prepared according to the customary methods.

For injection, the composition may be provided in the form of aqueous or oily lotions or in serum form. For the eyes, it may be provided in the form of drops, and for ingestion, it may be provided in the form of capsules, granules, syrups or tablets.

The quantities of the various constituents of the compositions according to the invention may be those conventionally used in the fields considered.

In the cosmetic field, these compositions constitute in particular cleansing, protective, treatment or care creams for the face, for the hands, for the feet, for the large anatomical folds and for the body (for example day creams, night creams, makeup-removing creams, foundation creams, anti-sun creams), fluid foundations, makeup-removing milks, protective or care body milks, anti-sun milks, lotions, gels or foams for skincare, such as cleansing lotions, artificial tanning lotions, bath compositions, deodorant compositions comprising a bactericidal agent, aftershave gels or lotions, compositions against insect bites, compositions for treating certain diseases of the skin such as eczema, rosacea, psoriasis, lichens and severe pruritus.

The compositions according to the invention may also consist of solid preparations constituting cleansing soaps or cakes.

The compositions may also be packaged in the form of an aerosol composition also comprising a pressurized propellant.

A composition according to the invention may also be a composition for care of the scalp, and in particular a shampoo, a hair-setting lotion, a treatment lotion, a hair-styling cream or gel, restructuring lotions for the hair, an anti-hair-loss lotion or gel, an antiparasitic shampoo, an antidandruff shampoo and the like.

A composition may also be for buccodental use, for example a toothpaste. In this case, the composition may contain customary adjuvants and additives for compositions for oral use, and in particular surfactants, thickening agents, humectants, polishing agents such as silica, various active ingredients such as fluorides, in particular sodium fluoride, and optionally sweetening agents such as sodium saccharinate.

When the composition is an emulsion, the proportion of the fatty phase may vary from about 5% to 80% by weight, and preferably from about 5% to 50% by weight relative to the total weight of the composition. The oils, waxes, emulsifiers and coemulsifiers used in the composition in the form of an emulsion are chosen from those conventionally used in the cosmetic field. The emulsifier and the coemulsifier are present in the composition in a proportion ranging from 0.3% to 30% by weight, and preferably from 0.5% to 20% by weight relative to the total weight of the composition. The emulsion may additionally contain lipid vesicles.

When the composition is an oily solution or gel, the fatty phase may represent more than 90% of the total weight of the composition.

In a known manner, the cosmetic composition may also contain customary adjuvants in the cosmetic field, such as hydrophilic or lipophilic gelling agents, hydrophilic or lipophilic additives, preservatives, antioxidants, solvents, perfumes, fillers, screening agents, odour absorbers and colouring matter. The quantities of these various adjuvants are those conventionally used in the cosmetic field, and for example vary from about 0.01% to 10% of the total weight of the composition. These adjuvants, according to their nature, may be introduced into the fatty phase, into the aqueous phase and/or into the lipid spherules.

As oils or waxes which can be used in the invention, there may be mentioned mineral oils (liquid paraffin), vegetable oils (liquid fraction of shea butter, sunflower oil), animal oils (perhydrosqualene), synthetic oils (Purcellin oil), silicone oils or waxes (cyclomethicone) and fluorinated oils (perfluoropolyethers), beeswax, carnauba wax or paraffin wax. It is also possible to add fatty alcohols and fatty acids (stearic acid) to these oils. As emulsifiers that can be used in the invention, there may be mentioned glyceryl stearate, polysorbate 60 and the PEG-6/PEG-32/Glycol Stearate mixture sold under the name Tefose® 63 by the company Gattefosse.

As solvents which can be used in the invention, there may be mentioned lower alcohols, in particular ethanol and isopropanol, and propylene glycol.

As hydrophilic gelling agents which can be used in the invention, there may be mentioned carboxyvinyl polymers (Carbomer®), acrylic copolymers such as copolymers of acrylates/alkyl acrylates, polyacrylamides, polysaccharides such as hydroxypropylcellulose, natural gums and clays, and, as lipophilic gelling agents, there may be mentioned modified clays such as bentones, metal salts of fatty acids such as aluminium stearates, hydrophobic silica, ethylcellulose and polyethylene.

The compounds of formula (I) may be used alone or as a mixture in any proportion.

According to one of the embodiments of the invention, they are used as sole desquamating agents.

According to another embodiment of the invention, they are used in combination with at least one other desquamating agent. The composition then contains at least one other desquamation-stimulating agent different from the compounds of formula (I).

The compounds of formula (I) promote the activity of other agents, whose quantity may thus be less in the composition.

The expression "desquamating agent" is understood to mean any compound capable of acting:
either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of Saphora japonica; resveratrol and some derivatives of jasmonic acid;
or on the enzymes involved in the desquamation or the degradation of the corneodesmosomes, glycosidases, stratum corneum chymotryptic enzyme (SCCE) of even other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, those described in the documents FR 2 570377, EP199636, EP325540, EP402072, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP1529522.

The compositions according to the invention may also contain other enzymes and in particular exogenous proteases, and/or glycosidases and/or lipases and/or amidases.

Such compounds are conventionally used in compositions intended for desquamating and/or accelerating the renewal of the horny layer, and combination with at least one compound of formula (I) as defined above will make it possible to strengthen and/or prolong their action. These enzymes, in particular proteases, will thus be effective at concentrations below those recommended when they are used in compositions without potentiating agent, which will limit the risks and difficulties linked to their use.

These proteases may be of animal, plant or microbiological origin, and are used in increasingly purified form. It is possible in particular to use proteases of microbiological origin, such as subtillisin, marketed under the name Exfocellia from COLETICA and Prozimex HTB LS 9142 from LS, or those commercially available under the trade names Neutrase® and Esperase® sold by the company NovoNordisk; these proteases may also be proteases present in plant extracts such as pawpaw, melon, and in particular based on papain, such as the product Linked Papain C-PS from COLLABORATIVE LABS, papain and bromelain, such as the product Vegeles LS2938 from LS, or Mucor mehi extract, such as Acitzyme E3M-M from ACTIVE ORGANICS.

The concentrations of these enzymes will be adjusted according to the degree of purity and the activity of the product containing them. They are generally from 0.0001% to 5%, but may be reduced to concentrations of less than or equal to 1%, or even less than or equal to 0.1%, in combination with compounds of formula I according to the invention.

Glycosidases may be all the enzymes capable of having, as substrate, proteoglycans, glycolipids and in general glycoconjugates of the stratum corneum. Such enzymes are in particular heparanase, sialidases such as for example neuraminidases, mannosidases, galactosidases, glucosidases, N-acetylglucosaminidases, N-acetylgalactosaminidases, chondroitinases, glucuronidases or hyaluronidases, but also cellulases, as described for example in application WO 02/38122; in particular, it is possible to use N-glycanase, cellulases, β-glucosidase, β-galactosidase, N-acetylglucosaminidase and/or N-acetylgalactosaminidase. The glycosidases used in the compositions according to the invention may be purified from extracts of proteins synthesized by the cells of the stratum corneum or may be glycosidases naturally synthesized by microorganisms. They may also be recombinant glycosidases produced in a heterologous system. Examples of glycosidases used are those marketed by Calbiochem or by Roche. It is understood that these enzymes may be present in the compositions containing the compound of formula I alone or in combination, in particular combinations of 2 or 3 glycosidases.

Examples of amidase or hydrolase with amidase activity are the compounds EC 3.5.1.1 to EC 3.5.1.89 of the conventional nomenclature, among which are asparaginase, glutaminase, amidase, urease, aminoacylase, aspartoacylase, ceramidase, peptidylglutaminase, formamidase, pentanamidase, aspartylglucosaminidase AGA, described in application EP 1 438968.

As lipase which can be used, there may be mentioned, without limitation, the product SP144 marketed by the company NOVO.

The compositions according to the invention may additionally contain at least one cosmetic active agent which is a compound chosen from moisturizing agents, agents reducing or inhibiting the activity of harmful proteases, agents stimulating epidermal differentiation and antiseborrheic agents.

The expression "moisturizing agent" is understood to mean:
- either a compound acting on the barrier function, in order to maintain moisturization of the stratum corneum, or an occlusive compound. There may be mentioned ceramides, sphingoid-based compounds, lecithins, glycosphingolipids, phospholipids, cholesterol and its derivatives, phytosterols (stigmasterol, β-sitosterol, camposterol), essential fatty acids, 1,2-diacylglycerol, 4-chromanone, pentacyclic triterpenes such as ursolic acid, petroleum jelly and lanolin;
- or a compound directly increasing the water content of the stratum corneum, such as threalose and its derivatives, hyaluronic acid and its derivatives, glycerol, pentanediol, sodium pidolate, serine, xylitol, sodium lactate, glyceryl polyacrylate, ectoin and its derivatives, chitosan, oligo- and polysaccharides, cyclic carbonates, N-lauroylpyrrolidonecarboxylic acid, N-α-benzoyl-L-arginine; Hepes, or C-glycosidated derivatives, as described in WO 02/051828;
- or a compound activating the sebaceous glands such as steroid derivatives (including DHEA, its 7-oxidized and/or 17-alkylated derivatives and sapogenins), methyl dihydrojasmonate, and vitamin D and its derivatives. The latter category of compounds will be more particularly suitable for applications to mature, or even very mature, skins, for example in individuals over 55 or 60 years.

These compounds may represent from 0.001% to 30%, preferably from 0.01 to 20%, of the total weight of the composition according to the invention.

The agents stimulating epidermal proliferation or differentiation which are useful in the compositions according to the invention are more specifically active on the keratinocytes.

The agents stimulating proliferation of the keratinocytes, which can be used in the composition according to the invention, comprise in particular retinoids such as retinol and its esters, including retinyl palmitate; adenosine; phloroglucinol; extracts of nut cakes marketed by the company GATTEFOSSE; and extracts of Solanum tuberosum marketed by the company SEDERMA.

The agents stimulating the differentiation of the keratinocytes comprise, for example, minerals such as calcium; a lupin peptide extract such as that marketed by the company SILAB under the trade name Structurin®; sodium beta-sitosterylsulphate such as that marketed by the company SEPORGA under the trade name Phytocohesin®; and a water-soluble maize extract such as that marketed by the company SOLABIA under the trade name Phytovityl®; a peptide extract of *Voandzeia substerranea* such as that marketed by the company Laboratoires Sérobiologiques under the trade name Filladyn LS 9397®; and lignans such as sec-oisolariciresinol.

The composition may as such also contain 8-hexadecene-1,16-dicarboxylic acid, ecdysteroids such as ecdysterone and its derivatives, or vitamin D derivatives, and/or PPAR agonists.

The agents stimulating the proliferation of fibroblasts which can be used in the composition according to the invention may for example be chosen from plant proteins or polypeptides, extracted in particular from soyabean (for example a soyabean extract marketed by the company LSN under the name Eleseryl SH-VEG 8® or marketed by the company SILAB under the trade name Raffermine®); and plant hormones such as giberrelins and cytokinins.

As agents reducing or inhibiting the activity of harmful proteases, there may be mentioned those acting
- either on the inhibition of metalloproteinases (matrix metalloproteinases or MMPs) such as more particularly MMPs 1, 2, 3 and 9. There may be mentioned: retinoids and derivatives, oligopeptides and lipopeptides, lipoamino acids, malt extract marketed by the company COLETICA under the trade name Collalift®; bilberry and rosemary extracts; lycopene; isoflavones, their derivatives or plant extracts containing them, in particular extracts of soyabean (marketed for example by the company ICHIMARU PHARCOS under the trade name Flavosterone SB®), red clover (marketed for example by the company SEDERMA under the name "STEROCARE®"), FLAX, kakkon or sage; Cucurma longa extracts; Siegesbeckla extracts (marketed for example by the company Sederma);
- or on the inhibition of certain serine proteases such as leukocyte elastase or cathepsin G. There may be mentioned: the peptide extract of legume (*Pisum sativum*) seeds marketed by the Laboratoires Sérobiologiques under the trade name Parelastyl®; heparinoids; and pseudodipeptides such as {2-[acetyl-(3-trifluoromethylphenyl)amino]-3-methylbutyrylamino}-acetic acid.

Other protease-inhibiting agents which may be added according to the invention are plasminogen activation inhibitors such as for example tranexamic acid.

Indeed, while certain protease activities may be advantageously activated according to the invention, it is known that other enzymes have a deleterious effect on the constituents of the dermis or of the epidermis and their activity must be repressed in order to obtain an optimum effect on the appearance and radiance of the skin.

According to another aspect, the composition contains antiseborrhoeic agents, and for example a 5α-reductase inhibitor; they may be chosen in particular from:
- retinoids, and in particular retinol;
- sulphur and sulphur-containing derivatives;
- zinc salts such as zinc lactate, gluconate, pidolate, carboxylate, salicylate and/or cysteate;
- selenium chloride;
- vitamin B6 or pyridoxin;
- the mixture of caprylol glycine, sarcosine and extract of *Cinnamomum zeylanicum* marketed in particular by the company SEPPIC under the trade name Sepicontrol A5®;
- an extract of *Laminaria saccharina* marketed in particular by the company Biotech Marine under the trade name Phlorogine®;
- an extract of *Spiraea ulmaria* marketed in particular by the company SILAB under the trade name Sebonormine®;
- extracts of plants of the species *Arnica montana, Cinchona succirubra, Eugenia caryophyllata, Humulus lupulus, Hypericum perforatum, Mentha piperita, Rosmarinus officinalis, Salvia officinalis* and *Thymus vulgaris*, all marketed for example by the company MARUZEN;
- an extract of *Serenoa repens* marketed in particular by the company EUROMED;
- extracts of plants of the genus *Silybum*; and
- extracts of *Eugenia caryophyllata* containing eugenol and eugenyl glucoside.

The compositions containing such agents will be more particularly intended for the treatment of oily or hyperseborrhoeic skins.

The subject of the invention is also a method of cosmetic treatment for promoting desquamation or for promoting the removal of the superficial layers of the skin and/or the superficial body growths comprising a step during which at least one compound of formula (I), in particular N-(2-hydroxyethyl)urea or a composition containing it, is applied to the area to be treated.

Another subject of the invention is a method of cosmetic treatment for promoting the radiance of the complexion and/or reducing the surface irregularities of the skin and/or the mucous membranes, wherein at least one compound of formula (I) or a composition as described in the preceding text is applied to the skin or the mucous membranes.

To carry out this method, the compound of formula (I) or the composition containing it may be applied to any area of the skin or of its annexes, in particular of the face, the neck and shoulders, the hands or to the lips, in order to smooth the visible and/or tactile irregularities of the skin, for example in order to tone down pigmented spots or scars, to smooth the surface and/or remove dead skins in particular from the lips.

The application times will vary according to the concentration of the compound of formula (I) in the composition, and the desired effect. As a guide, the composition may remain in contact with the skin or the superficial body growths between 5 min and 12 h, and may or may not be removed at the end of this contact time. The application may be carried out daily or twice daily, or weekly, and repeated during periods of 2 weeks to 6 months; it being possible to extend or renew this period with no difficulty.

According to another embodiment, the invention relates to a cosmetic method for promoting desquamation of the skin and/or the mucous membranes, comprising at least a step (i) of preparing the skin for peeling, consisting in applying to the areas to be treated at least one compound of formula (I) as defined in the preceding text, in particular N-(2-hydroxyethyl)urea, or its salts or its solvates, at a concentration at least less than that causing desquamation, and (ii) a subsequent step comprising the application of at least one desquamating agent at a suitable concentration to cause desquamation. A step for removing the desquamating agent(s) by rinsing will then be carried out.

Advantageously, the step (i) may be repeated with increasing concentrations of compound of formula (I). These concentrations will be adjusted by persons skilled in the art according to the desired effect and the number of applications envisaged, but will be generally less than 10%. It will be possible for example to use a first concentration of about 2%, and then one or more successive applications with a concentration of about 4%, and then 6 or 8% by weight.

Step (ii) comprises the application of at least one desquamating agent which may be chosen from the group comprising the compounds of formula (I) alone or as a mixture, in particular N-(2-hydroxyethyl)urea, but also sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; and (N-2-hydroxyethylpiperazine-N-2-ethane)sulphonic acid (HEPES), β-hydroxy acids such as salicylic acid and its derivatives, retinol and its esters, retinal, retinoic acid and its derivatives, chestnut or prickly pear extracts, reducing compounds such as cysteine or cysteine precursors, nicotinic acid and its esters and nicotinamide, also called vitamin B3 or vitamin PP, 8-hexadecene-1,16-dicarboxylic acid.

During step (ii), the desquamating agent(s) will be applied at a total concentration greater than or equal to 10%, in particular of about 20 to 50%, and will be left in contact with the skin for between 5 min and 6 hours, preferably for between 5 min and 30 min.

The method according to the invention comprises at least one additional step for removing the desquamating agent, in particular the compound of formula (I) such as N-(2-hydroxyethyl)urea by rinsing with water or with the aid of a mild detergent.

According to a particular embodiment, the invention relates to a method for the cosmetic treatment of keratin materials which consists in the application of at least two components:
  a first component comprising at least one compound of formula (I) or a composition containing it, as defined above,
  a second component comprising at least one agent chosen from proteases, lipases and glycosidases, these two components being applied simultaneously, conjointly or sequentially to the skin, the mucous membranes or the superficial body growths.

Advantageously, the second component will comprise at least one protease, involved in desquamation.

Agents chosen from moisturizing agents, agents reducing or inhibiting the activity of harmful proteases, agents stimulating epidermal differentiation and anti-seborrhoeic agents may advantageously be present in the first and/or the second component.

The first component may optionally contain at least one desquamating agent, such as those chosen from compounds directly promoting desquamation and compounds acting on the enzymes involved in desquamation or the degradation of the corneodesmosomes, in particular cysteine or its precursors.

A subject of the invention is therefore also a cosmetic composition or agent in the form of a kit comprising at least two components
  a first component comprising at least one compound of formula (I) as defined above,
  a second component comprising at least one agent chosen from proteases, lipases and glycosidases, these two components being intended to be applied simultaneously, conjointly or sequentially to the skin, the mucous membranes or the superficial body growths.

The additional desquamating agents described above, such as sulphonic acids, calcium chelators, α-hydroxy acids such as glycolic, citric, lactic, tartaric, malic or mandelic acids; ascorbic acid and its derivatives such as ascorbyl glucoside and magnesium ascorbyl phosphate; nicotinamide; urea; and (N-2-hydroxyethylpiperazine-N-2-ethane)sulphonic acid (HEPES), β-hydroxy acids such as salicylic acid and its derivatives, retinol and its esters, retinal, retinoic acid and its derivatives, chestnut and prickly pear extracts, reducing compounds such as cysteine or cysteine precursors, nicotinic acid and its esters and nicotinamide, also called vitamin B3 or vitamin PP, 8-hexadecene-1,16-dicarboxylic acid may also be present in the first and/or second component.

The first and/or second component may additionally comprise at least one cosmetic active agent as described in the preceding text, for example moisturizing agents, agents reducing or inhibiting the activity of harmful proteases, agents stimulating epidermal differentiation and antiseborrhoeic agents.

The subject of the invention is also a cosmetic or dermatological composition comprising at least one compound of formula (I) and at least one desquamating agent different from a compound of formula (I) as defined in the preceding text.

According to another aspect, the invention also relates to a cosmetic set comprising:
i) a container delimiting at least one compartment, the said container being closed with a closing element; and
ii) a composition as described above and placed inside the said compartment.

The container may be in any suitable form. It may be in particular in the form of a bottle, a tube, a pot, a box, a pack, a bag or a case.

The closing component may be in the form of a removable stopper, a cover, a lid, a tear-off strip or a capsule, in particular of the type comprising a body attached to the container and an articulated cap attached to the body. It may also be in the form of a component allowing selective closure of the container, in particular a pump, a valve or a shutter.

The container may be combined with an applicator, in particular in the form of a brush comprising an arrangement of bristles held together by a twisted wire. Such a twisted brush is described in particular in U.S. Pat. No. 4,887,622. It may also be in the form of a comb containing a plurality of application components obtained in particular from moulding. Such combs are described for example in patent FR 2 796 529. The applicator may be in the form of a brush, as described for example in patent FR 2 722 380. The applicator may be in the form of a foam or elastomer block, a felt, or a spatula. The applicator may be free (powder puff or sponge) or integrally attached to a rod carried by the closing component, as described for example in U.S. Pat. No. 5,492,426. The applicator may be integrally attached to the container, as described for example in patent FR 2 761 959.

The product may be contained directly in the container, or indirectly. By way of example, the product may be placed on an impregnated support, in particular in the form of a wipe or a swab, and placed (individually or several of them) in a pack or in a bag. Such a support incorporating the product is described for example in application WO 01/03538.

The closing component may be coupled to the container by screwing on. Alternatively, the coupling between the closing component and the container is otherwise carried out by screwing on, in particular via a bayonet mechanism, by snap-fitting, tightening, welding, adhesive bonding or by magnetic attraction. The expression "snap-fitting" is understood to mean in particular any system involving passing over a flange or a cord of material by elastic deformation of a portion, in particular of the closing component, and then by returning elastically to the stress-free position of the said portion after passing over the flange or the cord.

The container may be at least partially made of thermoplastic material. By way of example of thermoplastic material, there may be mentioned polypropylene or polyethylene.

Alternatively, the container is made of a non-thermoplastic material, in particular of glass or metal (or alloy).

The container may have rigid walls or deformable walls, in particular in the form of a tube or a tubulated bottle.

The container may comprise means intended to cause or facilitate the distribution of the composition. By way of example, the container may have deformable walls so as to cause the outflow of the composition in response to an over-pressure inside the container, which over-pressure is caused by elastic (or non-elastic) crushing of the walls of the container. Alternatively, in particular when the product is in the form of a stick, the latter may be driven by a piston mechanism. Still in the case of a stick, in particular for a makeup product, the container may comprise a mechanism, in particular with notches, or with a threaded rod, or with a helical ramp, and capable of moving a stick in the direction of the said opening. Such a mechanism is described for example in patent FR 2 806 273 or in patent FR 2 775 566. Such a mechanism for a liquid product is described in patent FR 2 727 609.

The container may consist of a case with a base delimiting at least one housing containing the composition, and a cover, in particular articulated to the base, and capable of at least partially covering the said base. Such a case is described for example in application WO 03/018423 or in patent FR 2 791 042.

The container may be equipped with a draining device in the vicinity of the container opening. Such a draining device makes it possible to wipe the applicator and optionally the rod to which it may be integrally attached. Such a draining device is described for example in patent FR 2 792 618.

The composition may be at atmospheric pressure inside the container (at room temperature) or pressurized, in particular by means of a propellant gas (aerosol). In the latter case, the container is equipped with a valve (such as those used for aerosols).

In one particular embodiment, the cosmetic set comprises at least (i) a first compartment containing at least one compound of formula (I) as defined above and (ii) a second compartment comprising at least one protease.

Another subject of the invention is the use of at least one compound of formula (I) as defined in the preceding text, for the preparation of reconstructed skins.

The invention thus relates to a method for extending the life of reconstructed skins in vitro, and more particularly of reconstructed epidermes.

According to one of the embodiments, the reconstructed epidermis may be treated with low concentrations of compounds of formula (I) such as N-(2-hydroxyethyl)urea and its derivatives, daily, in order to promote regular desquamation, similar to that observed in a healthy skin in vivo.

According to another aspect, the compound of formula (I), in particular N-(2-hydroxyethyl)urea, is applied to the reconstructed epidermis locally, at a high dose similar to those for peeling, that is about 20 to 40%, and then removed by rinsing; this method makes it possible to remove the constituted horny layer or a portion thereof, whose accumulation can damage the survival of the keratinocytes.

Another subject of the invention is a method for selecting desquamating molecules, comprising a step of determining the activation of proteases, in particular acid proteases, by the test compound.

This test comprises the steps consisting in:
a) preparing a stratum corneum extract containing acid proteases,
b) mixing a labelled protein substrate with various concentrations of the test compound, and with a proteolytic concentration of urea, in order to obtain mixtures comprising either the test compound, or urea
c) bringing fractions of the extract obtained in step a) into contact with the various mixtures obtained at the end of step b), in order to obtain reaction mixtures comprising either the test compound, or urea, or with the labelled casein substrate in order to obtain a control,
d) after an incubation time, comparing the proteolytic reaction in the various reaction mixtures with that of the control,
e) selecting the compound for which the intensity of proteolysis is greater than that of the control.

Advantageously, the extract of step a) is obtained by grinding of the stratum corneum, centrifuging and recovering the supernatant.

According to an advantageous embodiment, the protein substrate is a casein substrate. It may be labelled with a fluorescent group, which will be released during the proteolysis. It is in particular Bodipyfl-casein, which releases a fluorescence proportional to the proteolysis.

Other advantages of the invention will appear on reading the examples which follow.

Example 1

Degradation of Corneodesmosins in a Controlled Environment Chamber

The molecules are formulated in a neutral base Arlacel/Myrj. The products are in contact with varnished strippings under defined temperature, humidity and incubation time conditions. The corneodesmosin is assayed by immunodetection after incubation. It is studied on an immunoblot after electrophoretic separation and transfer onto a membrane. After specific labelling with the antibody G3619, it is visualized by chemiluminescence.

The Hydrovance® product, which is a mixture comprising N-(2-hydroxyethyl)urea marketed by the company National Starch, is compared with urea and with a control.

| Formulas | Formula No. |
|---|---|
| Base Arlacel/Myrj | 657236 |
| Base + 5% Hydrovance ® | 658890 |
| Base + 5% urea | 658892 |

Procedure:

Rectangles of 3×3.5 cm² are cut out in varnished strippings made on the bottom of dry skin legs. They are treated with 42 mg of product (4 mg/cm²) each. Controls and assays are carried out in parallel. The assays are incubated at 37° C. and 70% relative humidity for 5 days. The controls are kept for 5 days at −20° C. For each of the samples, acetone powders are made and weighed. The proteins are extracted with 100 µl of complete Laemmli buffer. They are assayed according to the Bradford method. The protein level of each sample is adjusted and will allow direct comparison of the various samples.

The proteins are separated by SDS-Page electrophoresis on 12% acrylamide gel. After transferring the proteins onto a PVDF membrane, the immunodetection is carried out with the anti-corneodesmosin antibody G3619 (Guy Serre) at 1/12 500 according to a conventional Western-blot technique. The visualization is performed by chemiluminescence. The bands detected by fluorSmax (Biorad) are quantified with the software quantity-one.

This experiment was repeated twice and during the second experiment, the immunoblots were performed in triplicate.

The results are a mean of 2 experiments performed.

Results:

The results are expressed as percentages of residual corneodesmosin relative to the control −80° C.

The lower the percentage, the higher the degradation and the higher the prodesquamating effect.

| | Mean of 2 experiments |
|---|---|
| Base Arlacel/Myrj | 79 |
| 5% Hydrovance | 23 |
| 5% urea | 30 |

Hydrovance® has a slightly higher effect than urea.

Example 2

"Keratolytic" Potential on the Proteins of the Stratum Corneum

Urea is known for its denaturing activity on keratolytic proteins. Optimization was performed in order to demonstrate a solubilization effect on keratins and proteins of the SC which are difficult to solubilize with urea derivatives.

Procedure:

30 mg of acetone powders of stratum corneum of the bottom of the legs of volunteers are prepared and brought into contact with 3 ml of water +2% CHAPS (zwitterionic detergent) for 10 min at room temperature. The mixture is then ground in a potter device and centrifuged for 10 min at 15 000 g. The supernatant is removed. This method makes it possible to remove the very soluble keratins and proteins which would interfere with the interpretation of the results. The pellet is taken up in 300 µl of water+CHAPS and 20 µl are distributed into 10 Eppendorf tubes.

Each molecule to be studied is prepared at 2M in water +2% CHAPS.

200 µl of solution are mixed with 20 µl of extract of acetone powders. The assays are carried out in duplicate. A control with no reagent is performed in parallel. The reaction mixtures are incubated for 10 min at room temperature, they are ground in a potter device and then incubated for 50 min at room temperature. They are centrifuged for 10 min at 15 000 g. The supernatants are collected and diluted ¼ in 1× Laemmli buffer. Electrophoresis is performed on a 12.5% acrylamide gel followed by staining with silver nitrate.

Results

The N-(2-hydroxyethyl)urea composition (Hydrovance®) is distinguishable from urea by the appearance of low MW bands; proteins that are better extracted or fragments generated during incubation.

Example 3

Activating Potential on Acid Proteases

Activation of Acid Proteases

The property of activating certain acid proteases of the SC (stratum corneum) is evaluated. The measurement of this activity is carried out by fluorimetric assay with the aid of the Enzchek kit (Molecular Probes). This protocol uses a Bodipyfl-casein substrate which, when hydrolysed, releases fluorescence. The fluorescence released is directly proportional to the protease activity. It is read directly on a 96-well plate in a spectrofluorimeter at 750V at an excitation of 485 nm and an emission of 535 nm.

The results obtained with N-(2-hydroxyethyl)urea (compound according to the invention) are compared with those for urea.

Procedure:

The molecules are prepared at 0, 1, 2 and 4 M in 0.1M acetic buffer; pH 5.0. An enzymatic extract is prepared from acetone powders. 2 ml of PBS buffer +0.1% Triton X100 are brought into contact for 1 h in crushed ice with 200 mg of stratum corneum acetone powders. The mixture is then ground in a potter device and then centrifuged for 10 min at 15 000 g at 4° C. The supernatant is collected. The Enzchek substrate diluted 1/200 is incorporated into each solution containing the molecules. The assays are repeated three times.

The reaction mixture is prepared directly in a white plate. 10 µl of enzymatic extract are added to 200 µl of solution containing the substrate at 0, 1, 2 or 4M. The readings are carried out at t0, 1 2 h, t 16 h and t 24 h.

Figure 1:
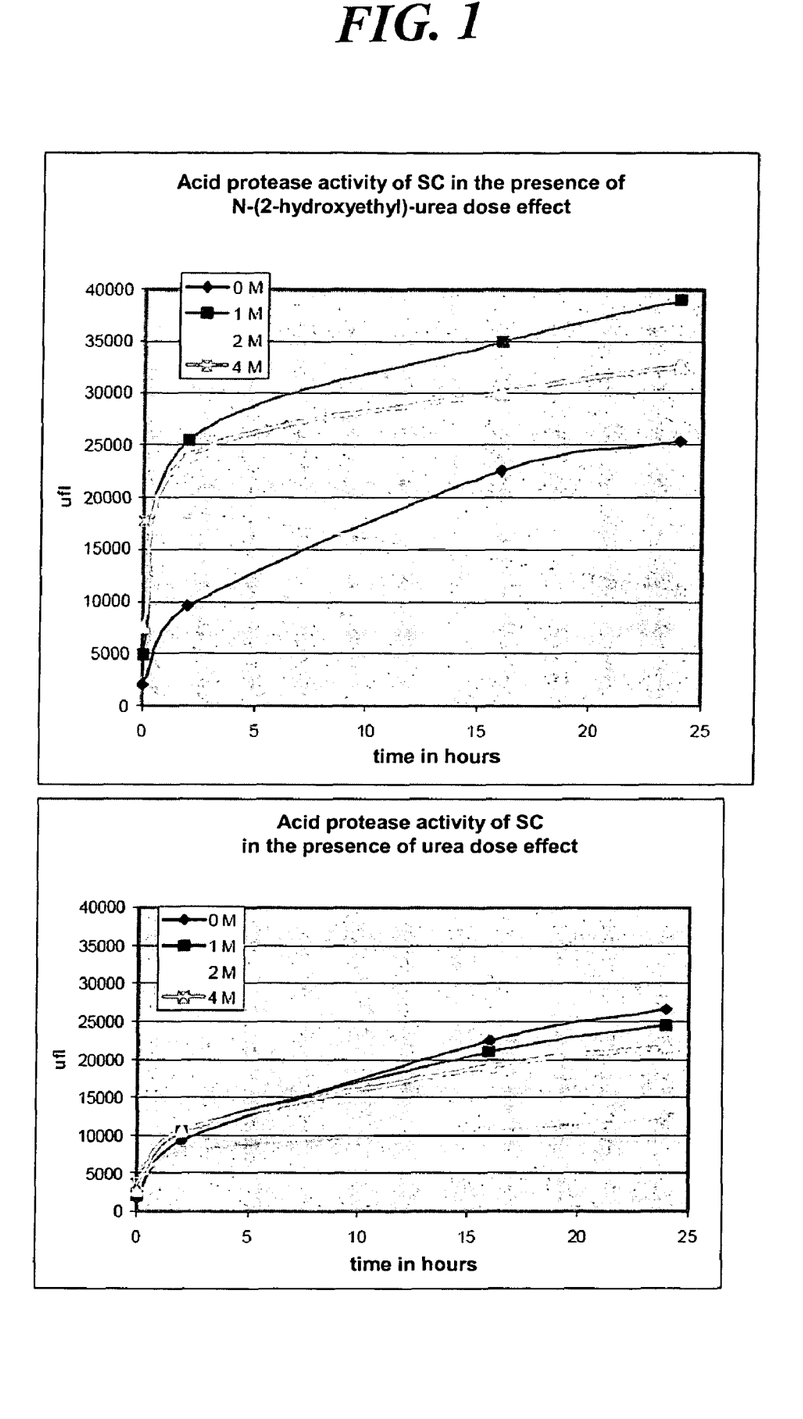
FIG. 1 shows the results of Example 3.

The results are represented in the appended FIGURE.

Urea at 1 and 2M has a slightly activating effect on acid proteases up to two hours after the start of incubation.

On the other hand, for Hydrovance® (N-(2-hydroxyethyl)urea), a large increase in activity is noted for concentrations of 1 and 2 M compared with the control. This increase is long-lasting. At 4M, a marked decrease in activity is observed regardless of the time studied.

Example 4

Compositions

| Care cream: | |
|---|---|
| TRIETHANOLAMINE | 0.3300 |
| WATER (and) HYDROXYETHYL UREA | 10.0000 |
| HYDROGENATED POLYISOBUTENE | 5.0000 |
| PROPYLPARABEN | 0.1000 |
| METHYLPARABEN | 0.2000 |
| CARBOMER | 0.3000 |
| CYCLOPENTASILOXANE | 15.0000 |
| WATER | 62.0700 |
| PEG-50 STEARATE | 2.5000 |
| GLYCERYL STEARATE (and) PEG-100 STEARATE | 2.5000 |
| CETYL ALCOHOL | 1.0000 |
| STEARYL ALCOHOL | 1.0000 |

The cream may be applied every night to the face and the neck.

| Formula with sugar esters | |
|---|---|
| WATER (and) HYDROXYETHYL UREA | 10.0000 |
| SHOREA ROBUSTA SEED BUTTER | 2.0000 |
| PRUNUS ARMENIACA (APRICOT) KERNEL OIL | 6.0000 |
| CHLORHEXIDINE DIGLUCONATE | 0.3000 |
| PROPYLPARABEN | 0.1000 |
| METHYLPARABEN | 0.2500 |
| XANTHAN GUM | 0.2500 |
| POLYACRYLAMIDE (and) C13-14 ISOPARAFFIN (and) LAURETH-7 | 1.0000 |
| CYCLOHEXASILOXANE | 10.0000 |
| WATER | 64.1000 |
| METHYL GLUCOSE SESQUISTEARATE | 2.0000 |
| PEG-20 METHYL GLUCOSE SESQUISTEARATE | 2.0000 |
| STEARYL ALCOHOL (and) CEREARTH-20 | 2.0000 |

The cream may be applied daily.

The above written description of the invention provides a manner and process of making and using it such that any person skilled in this art is enabled to make and use the same, this enablement being provided in particular for the subject matter of the appended claims, which make up a part of the original description and including the use of at least one compound of the following formula (I)

in which:

$R_1$, $R_2$, $R_3$ and $R_4$ each represent, independently of each other, a hydrogen atom, a $C_1$-$C_4$ alkyl group or a $C_2$-$C_6$ hydroxyalkyl group which may contain from 1 to 5 hydroxyl groups, where at least one of the radicals $R_1$ to $R_4$ represents a hydroxyalkyl group, and their salts, their solvates and their isomers; in a composition containing a physiologically acceptable medium, as agent intended for stimulating desquamation of the skin and/or the mucous membranes.

Further, description and enablement is provided herein for the following preferred embodiments of the invention:

1. Cosmetic use of at least one compound of the following formula (I)

in which:

$R_1$, $R_2$, $R_3$ and $R_4$ each represent, independently of each other, a hydrogen atom, a $C_1$-$C_4$ alkyl group or a $C_2$-$C_6$ hydroxyalkyl group which may contain from 1 to 5 hydroxyl groups, where at least one of the radicals $R_1$ to $R_4$ represents a hydroxyalkyl group, and their salts, their solvates and their isomers; in a composition containing a physiologically acceptable medium, as agent intended for stimulating desquamation of the skin and/or the mucous membranes.

2. Use of at least one compound of formula (I) according to Embodiment 1, characterized in that in formula (I) $R_1$ denotes a $C_2$-$C_6$ hydroxyalkyl group and $R_2$, $R_3$ and $R_4$ denote, independently of each other, a hydrogen atom or a $C_1$-$C_4$ alkyl group.

3. Use according to at least either of Embodiments 1 and 2, characterized in that in formula (I) $R_1$ denotes a $C_2$-$C_6$ hydroxyalkyl group comprising from 1 to 5 hydroxyl groups, and $R_2$, $R_3$ and $R_4$ denote a hydrogen atom.

4. Use according to at least one of Embodiments 1 to 3, characterized in that in formula (I) $R_1$ denotes a $C_2$-$C_6$ hydroxyalkyl group comprising 1 hydroxyl group.

5. Use according to at least one of Embodiments 1 to 4, characterized in that $R_1$ denotes a $C_2$-$C_4$ hydroxyalkyl group comprising 1 hydroxyl group and $R_2$, $R_3$ and $R_4$ denote a hydrogen atom.

6. Use according to at least one of Embodiments 1 to 5, characterized in that the compound of formula (I) is chosen from N-(2-hydroxyethyl)urea; N-(2-hydroxy-propyl)urea; N-(3-hydroxypropyl)urea; N-(2,3-dihydroxy-propyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-(tris-hydroxymethylmethyl)urea; N-ethyl-N'-(2-hydroxyethyl)urea; N,N-bis(2-hydroxyethyl)urea; N,N'-bis(2-hydroxyethyl)urea; N,N-bis(2-hydroxypropyl)urea; N,N'-bis(2-hydroxypropyl)urea; N,N-bis(2-hydroxyethyl)-N'- propylurea; N,N-bis(2-hydroxypropyl)-N'-(2-hydroxyethyl)urea; N-tert-butyl-N'-(2-hydroxyethyl)-N'-(2-hydroxypropyl)urea; N-(1,3-dihydroxy-2-propyl)-N'-(2-hydroxyethyl)urea; N,N-bis(2-hydroxyethyl)-N',N'-dimethylurea; N,N,N',N'-tetrakis(2-hydroxyethyl)urea; N',N'-bis(2-hydroxyethyl)-N',N'-bis(2-hydroxypropyl)-urea; and mixtures thereof.

7. Use according to at least one of Embodiments 1 to 6, characterized in that the compound of formula (I) is N-(2-hydroxyethyl)urea.

8. Use of at least one compound of formula (I) according to at least one of Embodiments 1 to 7, characterized in that the said compound stimulates the degradation of corneodesmosin.

9. Use according to at least one of Embodiments 1 to 8, characterized in that the compound of formula (I) has a keratolytic activity.

10. Use according to any one of the preceding Embodiments, characterized in that the compound of formula (I) stimulates the activity of proteases of the stratum corneum, in particular acid proteases.

11. Use of at least one compound of formula (I) according to at least one of Embodiments 1 to 10, characterized in that the composition is an exfoliating composition.

12. Use according to any one of the preceding Embodiments, characterized in that the composition is intended for cleansing the skin and/or the scalp.

13. Use according to any one of the preceding Embodiments, characterized in that the composition is intended to improve the surface state of the skin and/or the lips.

14. Use of at least one compound of formula (I) as defined in any one of Embodiments 1 to 7, for the preparation of a composition intended for the treatment of the signs associated with desquamation disorders.

15. Use of at least one compound according to Embodiment 14, characterized in that the composition is intended for the treatment of at least one skin disorder chosen from ichthyosis, hyperkeratosis, xeroses, psoriasis, atopic dermatitis, acne and dandruff.

16. Use of at least one compound according to either of Embodiments 14 and 15, characterized in that the composition is intended for promoting wound healing.

17. Use according to at least one of Embodiments 1 to 16, characterized in that the composition is a cosmetic and/or dermatological composition for topical application to the skin and/or the mucous membranes and/or the superficial body growths.

18. Use of at least one compound of formula (I) according to any one of Embodiments 1 to 17, characterized in that the composition additionally contains at least one desquamation-stimulating agent different from the compounds of formula (I).

19. Use according to Embodiment 18, characterized in that the desquamation-stimulating agent different from the compounds of formula (I) is chosen from the group comprising sulphonic acids, calcium chelators, (X-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids chestnut or prickly pear extracts and reducing compounds such as cysteine or cysteine precursors.

20. Use of at least one compound of formula (I) according to at least one of the preceding Embodiments, characterized in that the composition additionally contains at least one compound chosen from proteases, glycosidases and lipases.

21. Use of at least one compound of formula (I) according to any one of the preceding Embodiments, characterized in that the composition additionally contains at least one compound chosen from moisturizing agents, agents reducing or inhibiting the activity of harmful proteases, agents stimulating epidermal differentiation and antiseborrhoeic agents.

22. Method of cosmetic treatment for promoting the radiance of the complexion and/or reducing the surface irregularities of the skin and/or the mucous membranes, characterized in that at least one compound of formula (I) or a composition containing it according to any one of the preceding Embodiments is applied to the skin or the mucous membranes.

23. Method for the cosmetic treatment of keratin materials, characterized in that it comprises in the application of at least two components:
   a first component comprising at least one compound of formula (I) according to one of the preceding Embodiments,
   a second component comprising at least one agent chosen from proteases, lipases and glycosidases, these two components being applied simultaneously, conjointly or sequentially to the skin, the mucous membranes or the superficial body growths.

24. Method of cosmetic treatment according to the preceding Embodiment, characterized in that at least one compound chosen from moisturizing agents, agents reducing or inhibiting the activity of harmful proteases, agents stimulating epidermal differentiation, antiseborrhoeic agents and desquamating agents, is additionally present in the first and/or the second component.

25. Cosmetic agent in the form of a kit comprising at least two components
   a first component comprising at least one compound of formula (I) according to one of the preceding Embodiments,
   a second component comprising at least one agent chosen from proteases, lipases and glycosidases, these two components being applied simultaneously, conjointly or sequentially to the skin, the mucous membranes or the superficial body growths.

26. Cosmetic set comprising:
   a) a container delimiting at least one compartment, the said container being closed with a closing element; and
   b) a composition placed inside the said compartment, the composition conforming to any one of the preceding Embodiments.

27. Cosmetic set according to the preceding Embodiment, characterized in that it comprises at least (i) a first compartment containing at least one compound of formula (I) according to one of Embodiments 1 to 7 and (ii) a second compartment comprising at least one protease.

28. Use of at least one compound of formula (I) according to one of Embodiments 1 to 7, for the preparation of reconstructed skins.

29. Method for selecting desquamating compounds comprising the steps comprising in:
   a) preparing a stratum corneum extract containing acid proteases,
   b) mixing a labelled protein substrate with various concentrations of the test compound, and with a proteolytic concentration of urea, in order to obtain mixtures comprising either the test compound, or urea
   c) bringing fractions of the extract obtained in step a) into contact with the various mixtures obtained at the end of step b), in order to obtain reaction mixtures comprising either the test compound, or urea, or with the labelled casein substrate in order to obtain a control, d) after an incubation time, comparing the proteolytic reaction in the various reaction mixtures with that of the control, e) selecting the compound for which the intensity of proteolysis is greater than that of the control.

As used herein, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The invention method and composition is preferably used by subjects desirous of the benefits noted herein, subjects "in need of" these benefits. Such subjects are typically suffering from signs associated with desquamation disorders, such as by self diagnosis or cosmetician or medical diagnosis, or are at recognized and appreciated risk of developing such conditions and who use the invention methods and compositions to combat these effects. In this regard, the invention process can be viewed as one for delaying the onset of the appearance of, and/or for reducing signs associated with desquamation disorders. In this regard and for example, those interested in the invention use the compounds and compositions, etc. disclosed herein as agents intended for stimulating desquamation of the skin and/or the mucous membranes and/or the superficial body growths and the application in all cases where it is desirable to promote and/or accelerate the removal of the dead layers of the epidermis. This use is typically aimed at improving the physical appearance and/or the aesthetic appearance of the individual whose desquamation and/or exfoliation and/or cell renewal is being stimulated.

Naturally, one using the invention as disclosed will use an amount of the invention composition effective to reduce signs associated with desquamation disorders. Such amount is inclusive of an amount of the compositions described herein at the disclosed concentrations of active ingredients sufficient to cover the area of the skin being treated in a single application, and of course includes that amount applied upon repeated application, for example on a daily basis over a course of days, weeks, etc. In a preferred embodiment the invention process includes multiple applications of the invention composition to the area(s) of skin, etc. in need of attention. All of such amounts are "effective amounts."

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A method for treatment of skin suffering from ichthyosis, comprising:

stimulating natural desquamation of the skin suffering from ichthyosis by:

applying to the skin suffering from ichthyosis a composition, comprising:

a physiologically acceptable medium and a desquamation effective amount of at least one compound of the following formula (I)

wherein $R_1$, $R_2$, $R_3$ and $R_4$ each represent, independently of each other, a hydrogen atom, a $C_1$-$C_4$ alkyl group or a $C_2$-$C_6$ hydroxyalkyl group which may contain from 1 to 5 hydroxyl groups, where at least one of the radicals $R_1$ to $R_4$ represents a $C_2$-$C_6$ hydroxyalkyl group, their salts, their solvates, and mixtures thereof;

wherein the desquamation effective amount of the compound of formula (I) is from 1M to 4M, and is effective for stimulating the acid protease proteolytic activities of the stratum corneum.

2. The method according to claim 1, wherein in formula (I) $R_1$ is a $C_2$-$C_6$ hydroxyalkyl group and $R_2$, $R_3$ and $R_4$ are, independently of each other, a hydrogen atom or a $C_1$-$C_4$ alkyl group.

3. The method according to claim 1, wherein in formula (I) $R_1$ is a $C_2$-$C_6$ hydroxyalkyl group comprising from 1 to 5 hydroxyl groups, and $R_2$, $R_3$ and $R_4$ are each a hydrogen atom.

4. The method according to claim 1, wherein in formula (I) $R_1$ is a $C_2$-$C_6$ hydroxyalkyl group comprising 1 hydroxyl group.

5. The method according to claim 1, wherein $R_1$ is a $C_2$-$C_4$ hydroxyalkyl group comprising 1 hydroxyl group and $R_2$, $R_3$ and $R_4$ are each a hydrogen atom.

6. The method according to claim 1, wherein the compound of formula (I) is selected from the group consisting of N-(2-hydroxyethyl)urea, N-(2-hydroxypropyl)urea, N-(3-hydroxypropyl)urea, N-(2,3-dihydroxypropyl)urea, N-(2,3,4,5,6-pentahydroxyhexyl)urea, N-methyl-N-(1,3,4,5,6-pentahydroxy-2-hexyl)urea, N-methyl-N'-(1-hydroxy-2-methyl-2-propyl)urea, N-(1-hydroxy-2-methyl-2-propyl)urea, N-(1,3-dihydroxy-2-propyl)urea, N-(tris-hydroxymethylmethyl)urea, N-ethyl-N'-(2-hydroxyethyl)urea, N,N-bis(2-hydroxyethyl)urea, N,N'-bis(2-hydroxyethyl)urea, N,N-bis(2-hydroxypropyl)urea, N,N'-bis(2-hydroxypropyl)urea, N,N-bis(2-hydroxyethyl)-N'-propylurea; N,N-bis(2-hydroxypropyl)-N'-(2-hydroxyethyl)urea, N-tert-butyl-N'-(2-hydroxy-ethyl)-N'-(2-hydroxypropyl)urea, N-(1,3-dihydroxy-2-propyl)-N'-(2-hydroxyethyl)urea, N,N-bis(2-hydroxyethyl)-N',N'-dimethylurea, N,N,N',N'-tetrakis(2-hydroxyethyl)urea, N',N'-bis(2-hydroxyethyl)-N',N'-bis(2-hydroxypropyl)urea, salts thereof, solvates thereof, and mixtures thereof.

7. The method according to claim 1, wherein the at least one compound of formula (I) is N-(2-hydroxyethyl)urea.

8. The method according to claim 1, wherein the compound of formula (I) stimulates the degradation of corneodesmosin.

9. The method according to claim 1, wherein the compound of formula (I) has keratolytic activity.

10. The method according to claim 1, wherein the composition is an exfoliating composition.

11. The method according to claim 1, wherein the composition further comprises at least one desquamation-stimulating agent not a compound of formula (I).

12. The method according to claim 11, wherein the desquamation-stimulating agent not a compound of formula (I) is at least one selected from the group consisting of sulphonic acids, calcium chelators, α-hydroxy acids, ascorbic acid, ascorbyl glucoside, magnesium ascorbyl phosphate, nicotinamide; urea; (N-2-hydroxyethylpiperazine-N-2-ethane)sulphonic acid (HEPES), β-hydroxy acids, retinoids, chestnut or prickly pear extracts, cysteine, cysteine precursors, and mixtures thereof.

13. The method according to claim 1, wherein the composition further comprises at least one compound chosen from proteases, glycosidases and lipases.

14. The method of claim 1, further comprising application to the skin suffering from ichthyosis:
a second component comprising at least one agent chosen from proteases, lipases and glycosidases,
these second component being applied simultaneously, conjointly or sequentially relative to compound of formula (I) to the skin suffering from ichthyosis.

15. The method according to claim 1, further comprising applying to the skin suffering from ichthyosis, a second composition comprising a physiologically acceptable medium and an increased concentration of at least one compound of formula (I) relative to the first application.

16. The method according to claim 1, further comprising, after applying the composition to the skin suffering from ichthyosis:
removing the composition by rinsing with water or with a mild detergent.

17. The method according to claim 1, wherein a weight % of the at least one compound of formula (I) is 20-40 wt. %.

18. A kit comprising at least two compositions, wherein a first comprises:
a physiologically acceptable medium and
a desquamation effective amount of at least one compound of formula (I)

wherein:
$R_1$, $R_2$, $R_3$ and $R_4$ each represent, independently of each other, a hydrogen atom, a $C_1$-$C_4$ alkyl group or a $C_2$-$C_6$ hydroxyalkyl group which may contain from 1 to 5 hydroxyl groups, where at least one of the radicals $R_1$ to $R_4$ represents a hydroxyalkyl group, their salts, their solvates, and mixtures thereof, wherein
the desquamation effective amount of the compound of formula (I) is from 1M to 4M, and is effective for stimulating the acid protease proteolytic activities of the stratum corneum; and
a second composition comprising at least one agent selected from the group consisting of proteases, lipases and glycosidases.

* * * * *